(12) United States Patent
Maeda et al.

(10) Patent No.: US 7,325,924 B2
(45) Date of Patent: Feb. 5, 2008

(54) OPHTHALMIC PHOTOGRAPHIC APPARATUS

(75) Inventors: Naoki Maeda, Takamatsu (JP); Kazunori Matsumura, Hamamatsu (JP); Shigeru Takimoto, Hamamatsu (JP)

(73) Assignees: Kowa Company Ltd. (JP); RyuSyo Industrial Co., Ltd. (JP)

( * ) Notice: Subject to any disclaimer, the term of this patent is extended or adjusted under 35 U.S.C. 154(b) by 690 days.

(21) Appl. No.: 10/739,968

(22) Filed: Dec. 18, 2003

(65) Prior Publication Data

US 2005/0018135 A1   Jan. 27, 2005

(30) Foreign Application Priority Data

Dec. 27, 2002  (JP) .............................. 2002-378859

(51) Int. Cl.
*A61B 13/14*   (2006.01)
(52) U.S. Cl. ........................................ 351/206; 351/208
(58) Field of Classification Search ........ 351/200–208, 351/221–223, 243
See application file for complete search history.

(56) References Cited

U.S. PATENT DOCUMENTS 4,423,931 A * 1/1984 Shapiro ...................... 351/206
4,762,410 A * 8/1988 Sekiguchi et al. .......... 351/206

\* cited by examiner

*Primary Examiner*—M. Hasan
(74) *Attorney, Agent, or Firm*—Adams & Wilks

(57) ABSTRACT

An ophthalmic photographic apparatus comprises a photographic mask for defining a fundus photography range, a photographic stop for eliminating light reflected from an anterior portion of the eye, and a focusing lens for bringing the fundus into focus. The photographic mask and the photographic stop are interlocked and move as one unit relative to the movement of the focusing lens in such a way that with respect to a photographic optical system, the photographic mask is maintained at a position substantially conjugate with an imaging plane of a CCD and the photographic stop is maintained at a position substantially conjugate with an anterior portion of the eye. The CCD is located at the image-side focal plane of the image-formation lens, the mask is located on the object-side focal plane of the focusing lens, and the photographic stop is located on the image-side focal plane of the focusing lens.

8 Claims, 1 Drawing Sheet

OPHTHALMIC PHOTOGRAPHIC APPARATUS

BACKGROUND OF THE INVENTION

1. Field of the Invention

The present invention relates to an ophthalmic photographic apparatus that uses electronic imaging means to photograph an image of a fundus of an eye to be examined.

2. Description of the Prior Art

A portable fundus camera is well known, generally either having a construction in which a part required for photographic operation such as at least part of the optical system used for observation and photography is separate, allowing it to be carried by the examiner, or a construction in which, if possible, all the camera components are housed in a case that can be carried. Japanese Patent Laid-open Publication No. 256726/92 describes the former type of fundus camera.

Because photographic images recorded by a fundus camera are used for making medical diagnoses, the images have to be reliable. For example, it is necessary to ensure that the images that are photographed do not include images of reflected light (flares) from the anterior portion of the eye. To achieve this purpose, extensive use is made of a structure in which, in the optical system, a photographic mask is disposed at a position that is conjugate with the eye fundus and a photographic stop is disposed at a position that is conjugate with the anterior portion of the eye.

It is desirable to make the above-described portable fundus cameras as light and compact as possible. To do that, it is desirable to use a very compact optical system and reduce the number of lenses used. To satisfy those conditions, the photographic mask is located on the film plane, which is to say, the final image-formation plane. This has made it unnecessary to separately provide a fundus-conjugate position that is on the image side of the focusing lens.

In recent years, moreover, fundus cameras are being used that record the fundus image as an electronic image. Utilizing an electronic photographic system makes it possible to make the camera apparatus smaller and lighter, to the extent that all the component parts can be housed in a case that is still light and small enough to be readily carried. Imaging devices used by these electronic cameras include CCD sensors and CMOS sensors.

However, because the imaging (image-formation) plane is not on the surface of the imaging device in the case of an electronic camera, it is very difficult to arrange the photographic mask at its imaging plane. If there was a desire to employ an imaging device that included a photographic mask on its imaging plane, it would be necessary to manufacture the imaging device incorporating the required mask that met the requisite size and other criteria beforehand, which would make the camera hardware very costly.

Thus, when imaging devices are used, it is necessary to provide a fundus-conjugate position somewhere else along the photographic optical path. In such a case, it is desirable that movements of the focusing lens made for adjustment in diopter of the eye to be examined have no influence on the size of the mask image on the imaging device. A fundus-conjugate position is therefore provided on the image side of the focusing lens for the photographic mask and additionally a relay lens and condenser lens are provided to form the image on the imaging device. If, however, the mask is provided on a fundus-conjugate position somewhere else between the focusing lens and the imaging plane, it would increase the length of the optical system, which, together with the need for a relay lens, makes it more difficult to achieve the light weight and small size that are the desirable attributes for a portable fundus camera.

An object of the present invention is therefore to provide an eye fundus photographic apparatus having an optical system that includes a photographic mask and a photographic stop and that is light and compact and can be readily fabricated at a low cost.

SUMMARY OF THE INVENTION

To attain the above object, the invention provides an ophthalmic photographic apparatus that uses electronic imaging means to photograph an image of a fundus of an eye to be examined, wherein interlocking means are provided to move a photographic mask for defining a fundus photography range and/or a photographic stop for eliminating light reflected from an anterior portion of the eye in an interlocked manner relative to the movement of the focusing lens in such a way that with respect to a photographic optical system the photographic mask may be kept at a position substantially conjugate with an imaging plane of the electronic imaging means and/or the photographic stop may be kept at a position substantially conjugate with an anterior portion of the eye.

Further features of the invention, its nature and various advantages will be more apparent from the accompanying drawings and following detailed description of the invention.

DESCRIPTION OF THE PREFERRED EMBODIMENT

Figure 1:
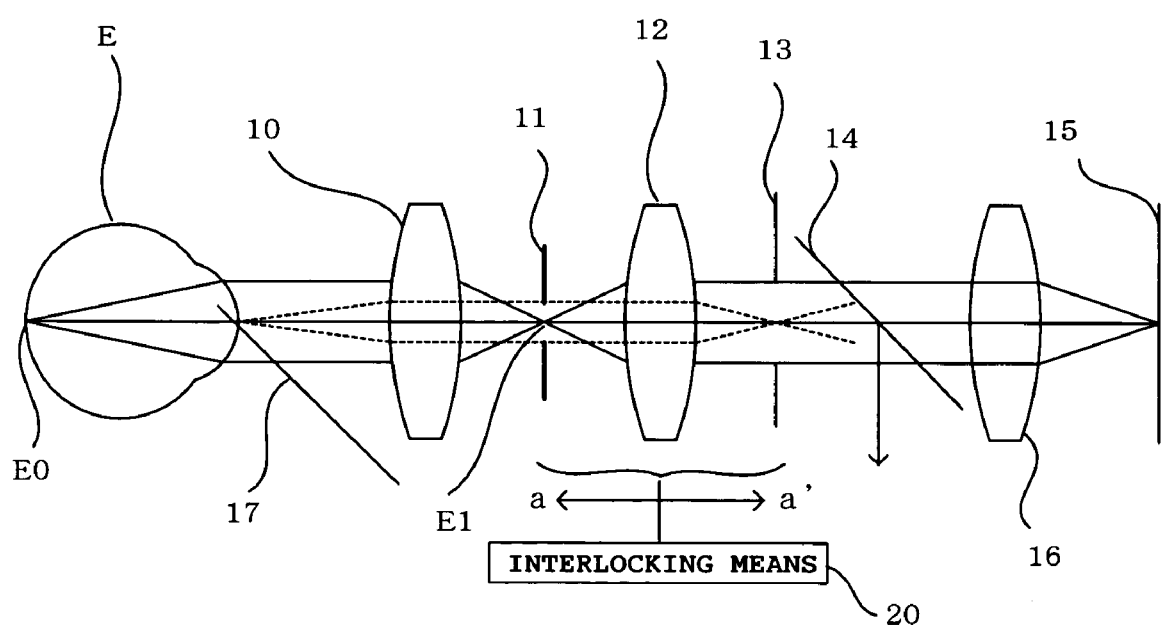
FIG. 1 is a diagram illustrating the configuration of the optical system of an eye fundus camera according to the present invention.

One embodiment of the present invention will now be described with reference to FIG. 1, which shows the optical system of an eye fundus camera. The fundus camera shown in FIG. 1 is a portable type that uses a CCD imaging device. However, it is to be understood that the invention is not limited to a CCD imaging device, but can use an imaging system based on other imaging devices such as a CMOS sensor or the like.

In FIG. 1, symbol E denotes the subject eye to be examined, and reference numerals 10 to 16 denote the parts that make up the optical system of the fundus camera. In the drawing, the optical system axis is coincident with the optical axis of the eye.

The illumination optical system axis 17 is shown to the front of an objective lens 10. The illumination optical system itself is not shown, but can be a conventional type used in existing portable fundus cameras in which optical means such as prisms are used to illuminate the anterior portion of the eye E with alignment set as shown. The illumination optical system axis 17 and the optical axis of the photographic optical system (hereinafter the "main optical system") are arranged so that they intersect in or near the vicinity of the focal point on the object side of the objective lens 10. The illumination optical system includes optical means (image-formation system) whereby the illuminating beam is at its smallest in the vicinity of the anterior portion of the eye E with the eye E in an aligned state, particularly with respect to the photographic distance, and the point at which the illuminating beam is at its smallest coincides with the entrance pupil of the photographic optical system. While specific-details of the illumination optical system are not shown, any system can be used that satisfies the above configuration.

With the eye E set in alignment, particularly with respect to the photographic distance, the object-side focal point of the objective lens 10 substantially coincides with the anterior portion of the eye. The main optical system shown in FIG. 1 has three lenses: the objective lens 10, a focusing lens 12 and an image-formation lens 16. A CCD 15 used to obtain an image of the eye fundus is located behind the image-formation lens 16.

Provided between the focusing lens 12 and the image-formation lens 16 is a return mirror 14 that is used to reflect the fundus image towards an eyepiece (not shown), making it possible for the examiner to observe the eye fundus. When a shutter button (not shown) is operated to issue a command to take a photograph, the return mirror 14 is retracted from the optical path of the main optical system, thereby causing the photography light to be guided to the CCD 15. To effect the retraction, the return mirror 14 uses a conventional drive mechanism that includes a spring or solenoid or the like.

A photographic mask 11 is used to define the range of the fundus image. Instead of being located on the imaging plane of the CCD 15, which is difficult to do, as described above, the mask 11 is provided at a location that is a conjugate of the imaging plane of the CCD 15, and the mask 11 is arranged in such a way that it is always kept at a position conjugate therewith. The simplest method for maintaining the mask 11 to be conjugate with the imaging plane of the CCD 15 is to provide between the focusing lens 12 and the image-formation lens 16 a telecentric optical system, in which a position conjugate with the imaging plane of the CCD 15 is brought to a fixed distance to the front of the focusing lens 12, which is the position at which the mask 11 is located. In other words, the CCD 15 is located on the image-side focal plane to the rear of the image-formation lens 16, and the mask 11 is located on the object-side focal plane to the front of the focusing lens 12.

In this arrangement, it is only necessary to have the mask 11 and focusing lens 12 moved as one by an interlocking means 20, whereby the mask 11 and focusing lens 12 are integrally moved along a line indicated in the drawing as a-a' in accordance with focusing adjustments made by the examiner. This means that regardless of the focusing adjustments made, the mask 11 is always maintained at a position that is conjugate with the imaging plane of the CCD 15.

To eliminate reflected light from the anterior portion of the eye, a photographic stop 13 is provided at a position conjugate with the anterior portion of the eye, and is constantly maintained at that position. For this, after making the requisite alignment, the photographic stop 13 is disposed behind the focusing lens 12 at a position that is conjugate with the anterior portion of the eye and the interlocking means 20 are used to move the photographic stop 13 integrally with the mask 11 and focusing lens 12.

The system is configured so that, when it is in alignment, the illumination optical system axis 17 intersects the main optical axis at the object-side focal point of the objective lens 10. In the state aligned, particularly with respect to the distance, the region in the vicinity of the anterior portion of the eye E substantially coincides with the vicinity of the focal plane on the object side of the objective lens 10. Therefore, the photographic stop 13 only needs to be aligned with the focal plane on the image side of the focusing lens 12. Depending on the alignment conditions with respect to the photographic distance to the eye E, the distance between the photographic stop 13 and the focal plane on the image side of the focusing lens 12 can be adjusted to achieve a more accurate conjugate relationship relative to the anterior portion of the eye, or to better eliminate light that is not required.

The mask 11, focusing lens 12 and photographic stop 13 can be integrated by using a lens-barrel or the like. The interlocking means 20 include manual or motorized driving means to move the mask 11, focusing lens 12 and photographic stop 13 along the line a-a' as an integral unit.

The positional relationship between the photographic stop 13 and the return mirror 14 does not have to be as shown in the drawing. However, locating the photographic stop 13 to the front of the return mirror 14 is advantageous in that it enables the photographic stop 13 to also be used for the observation optical system. As such, it is convenient to employ the illustrated positional relationship, using lenses with suitable powers.

With the above arrangement, the examiner views the eye fundus through an eyepiece (not shown) as he makes the required alignments with the eye E, which include aligning the axes of the main and illumination optical systems and the setting of the photographic distance. The examiner then adjusts the focus, using operating means (not shown) to move the mask 11, focusing lens 12 and photographic stop 13 as one unit in which the relative positional relationship of the component parts is maintained.

Any conventional system can be used to judge the focus. When the focusing has been completed, the conjugate position E1 of the eye fundus E0 relative to the objective lens 10 is in alignment with the position that is conjugate with the imaging plane of the CCD 15, where the mask 11 is located. At the same time, the photographic stop 13 will also be conjugate with the anterior portion of the eye E. When photography is then initiated by, for example, operating a shutter button (not shown), the photographic stop 13 ensures that the photographic area defined by the mask 11 is not affected by flares of light reflected from the anterior portion of the eye, thereby enabling the CCD 15 to take high-quality images of the eye fundus.

Because in the above configuration the photographic mask 11 is conjugate with the imaging plane of the CCD 15 and is maintained in that position regardless of whatever focusing adjustments that are made, the mask 11 does not have to be disposed on the imaging plane of the CCD 15. Also, it is not necessary to ensure that the position conjugate with the imaging plane of the CCD 15 is within the optical system using a relay lens. Thus, with fewer optical components, a simpler, lower-cost implementation is possible, enabling configuration of a portable fundus camera that is light and compact. Similarly, the photographic stop 13 is constantly maintained at a position that is conjugate with the anterior portion of the eye regardless of whatever focusing adjustments that are made, so that it can be ensured that unnecessary light from the anterior portion of the eye is always excluded.

In the above embodiment, regardless of the movement of the focusing lens 12 during the focusing operation, the photographic mask 11 is maintained at a position conjugate with the imaging plane of the CCD 15 with respect to the rear half of the main optical system constituted by the focusing lens 12 and the image-formation lens 16, and the photographic stop 13 is maintained at a position conjugate with the anterior portion of the eye with respect to the front half of the main optical system constituted by the objective lens 10 and the focusing lens 12. To accomplish this, an example has been shown of a structure that enables the mask 11, focusing lens 12 and photographic stop 13 to be moved as one unit with these components maintained in an equal distance to each other.

However, it is to be understood that, provided the above-described conjugate relationships of the mask 11 and photographic stop 13 are maintained regardless of whatever focusing adjustments are performed, the positional relationships of the focusing lens 12, mask 11 and photographic stop 13 need not be fixed. For example, a configuration could be employed in which helicoid and cam mechanisms and the like are used to effect dynamic adjustment.

Moreover, although the above embodiment was described with reference to a configuration in which the movement of the mask 11 and photographic stop 13 is interlocked with the movement of the focusing lens 12, the photographic stop 13 can be dispensed with if a configuration is used that does not require the use of a photographic stop. Even if that is done, the same type of effect can still be attained with respect to the mask 11 that is left.

As described in the foregoing, an ophthalmic photographic apparatus according to the invention uses electronic imaging means to photograph an image of a fundus of an eye to be examined, wherein interlocking means are provided to move an photographic mask for defining a fundus photography range and/or a photographic stop for eliminating light reflected from an anterior portion of the eye in such a way that with respect to a photographic optical system the photographic mask may be kept at a position substantially conjugate with an imaging plane of the electronic imaging means and/or the photographic stop may be kept at a position substantially conjugate with an anterior portion of the eye. The invention thus makes it possible to inexpensively and readily configure a light, compact optical system for a fundus camera that includes a photographic mask and a photographic stop.

What is claimed is:

1. An ophthalmic photographic apparatus that uses electronic imaging means to photograph an image of a fundus of an eye to be examined, comprising:
    a photographic mask for defining a fundus photography range;
    a photographic stop for eliminating light reflected from an anterior portion of the eye;
    a focusing lens for bringing the fundus into focus; and
    interlocking means for moving the photographic mask and the photographic stop in an interlocked manner relative to the movement of the focusing lens in such a way that with respect to a photographic optical system the photographic mask is maintained at a position substantially conjugate with an imaging plane of the electronic imaging means and the photographic stop is maintained at a position substantially conjugate with an anterior portion of the eye.

2. An ophthalmic photographic apparatus that uses electronic imaging means to photograph an image of a fundus of an eye to be examined, comprising:
    a photographic mask for defining a fundus photography range;
    a focusing lens for bringing the fundus into focus; and
    interlocking means for moving the photographic mask in an interlocked manner relative to the movement of the focusing lens in such a way that with respect to a photographic optical system the photographic mask is maintained at a position substantially conjugate with an imaging plane of the electronic imaging means.

3. An apparatus according to claim 2, further comprising a photographic stop for eliminating light reflected from an anterior portion of the eye, said photographic stop being moved in an interlocking manner relative to the movement of the focusing lens in such a way that with respect to a photographic optical system the photographic stop is maintained at a position substantially conjugate with an anterior portion of the eye.

4. An apparatus according to claim 1, wherein the photographic mask is located on an object-side focal plane of the focusing lens.

5. An apparatus according to claim 1, wherein the photographic stop is located on an image-side focal plane of the focusing lens.

6. An apparatus according to claim 1, wherein the photographic optical system includes an objective lens to condense light from the eye being examined, and an image-formation lens to form an eye fundus image at the image-formation plane of the electronic imaging means, the focusing lens being located between the objective lens and the image-formation lens.

7. An apparatus according to claim 6, wherein the imaging plane of the electronic imaging means is located on an image-side focal plane of the image-formation lens.

8. An apparatus according to claim 6, wherein an optical axis of the illumination optical system used to illuminate the eye fundus and the optical axis of the photographic optical system intersect or come into close proximity in the vicinity of the object-side focal plane of the objective lens.

* * * * *